United States Patent
Smith, Jr. et al.

(10) Patent No.: US 9,139,503 B2
(45) Date of Patent: Sep. 22, 2015

(54) METHOD FOR THE PRODUCTION OF DIMETHYL ETHER

(75) Inventors: Lawrence A. Smith, Jr., Pasadena, TX (US); Abraham P. Gelbein, Raleigh, NC (US); Christopher C. Boyer, Houston, TX (US)

(73) Assignee: Lummus Technology Inc., Bloomfield, NJ (US)

( * ) Notice: Subject to any disclaimer, the term of this patent is extended or adjusted under 35 U.S.C. 154(b) by 1333 days.

(21) Appl. No.: 11/852,923

(22) Filed: Sep. 10, 2007

(65) Prior Publication Data

US 2009/0069607 A1    Mar. 12, 2009

(51) Int. Cl.
*C07C 41/01* (2006.01)
*C07C 41/09* (2006.01)

(52) U.S. Cl.
CPC ..................................... *C07C 41/09* (2013.01)

(58) Field of Classification Search
None
See application file for complete search history.

(56) References Cited

U.S. PATENT DOCUMENTS

| | | | |
|---|---|---|---|
| 2,366,007 A | 12/1944 | D'Alelio | |
| 3,267,156 A | 8/1966 | Hansen | |
| 3,931,349 A | 1/1976 | Kuo | |
| 4,230,533 A | 10/1980 | Giroux | |
| 4,443,559 A | 4/1984 | Smith, Jr. | |
| 4,551,567 A | 11/1985 | Smith, Jr. | |
| 4,582,569 A | 4/1986 | Jenkins | |
| 4,629,710 A | 12/1986 | Smith, Jr. | |
| 4,826,574 A | 5/1989 | Gourlia et al. | |
| 5,037,511 A | 8/1991 | Dornhagen et al. | |
| 5,057,468 A | 10/1991 | Adams | |
| 5,262,012 A | 11/1993 | Smith, Jr. | |
| 5,266,546 A | 11/1993 | Hearn | |
| 5,316,627 A | 5/1994 | Hammer et al. | |
| 5,339,648 A | 8/1994 | Lockett et al. | |
| 5,348,710 A | 9/1994 | Johnson et al. | |
| 5,684,213 A | 11/1997 | Nemphos et al. | |
| 5,705,711 A | 1/1998 | Preston | |
| 5,730,843 A | 3/1998 | Groten et al. | |
| 5,755,933 A | 5/1998 | Ognisty et al. | |
| 6,369,280 B1 * | 4/2002 | Tamminen et al. | 568/697 |
| 6,740,783 B1 | 5/2004 | Jun et al. | |
| 7,026,517 B2 | 4/2006 | Groten et al. | |
| 2007/0066855 A1 | 3/2007 | Malandrino et al. | |

FOREIGN PATENT DOCUMENTS

DE    908247 C    4/1954

OTHER PUBLICATIONS

PCT International Search Report issued in PCT Application No. PCT/US2008/063881 dated Sep. 30, 2008 (3 pages).
PCT Written Opinion issued in PCT Application No. PCT/US2008/063881 dated Sep. 30, 2008 (5 pages).
Office Action (with translation) issued Dec. 15, 2010 in corresponding Ukrainian application a2010 03324 (6 pages).
Examiner's First Report issued Feb. 1, 2011 in corresponding Australian patent application No. 2008299809 (2 pages).
Official Action (w/translation) issued Feb. 1, 2013 in corresponding Eurasian application No. 201070357 (4 pages).
First Office Action issued Aug. 3, 2011 in corresponding Chinese application 200810083695.9 (9 pages).
Office Action issued Aug. 5, 2011 in corresponding Eurasian application 201070357 (4 pages).
Second Office Action issued Jun. 1, 2012 in corresponding Chinese application 200810083695.9 (7 pages).
Examiner's report issued Jul. 9, 2012 in corresponding Chilean Patent Application No. 1869-2008 (with letter summarizing the same) (12 pages).
Office Action (with translation) issued Apr. 23, 2012 in corresponding Eurasian application 201070357/28 (6 pages).
Correspondence reporting Office Action dated Aug. 3, 2012 issued in corresponding Indonesian Patent Application No. W-00201000770 (5 pages).
Notification of Readiness to Grant (w/translation) issued Oct. 22, 2013 in corresponding Eurasian application No. 201070357 (5 pages).
Examiner's report issued Feb. 1, 2013 in corresponding Chilean Patent Application No. 1869-2008 (with letter summarizing the same) (9 pages).

* cited by examiner

*Primary Examiner* — Rosalynd Keys
(74) *Attorney, Agent, or Firm* — Osha • Liang LLP

(57) ABSTRACT

A process for the production of dialkyl ether, the process including: feeding a stream comprising an alkyl alcohol to a distillation column reactor system; concurrently in the distillation column reactor system: i) contacting the alkyl alcohol with a catalytic distillation structure in a distillation reaction zone thereby catalytically reacting at least a portion of the alkyl alcohol to form a corresponding dialkyl ether and water; and ii) fractionating the resulting dialkyl ether from the water; operating the distillation column reactor system to obtain substantially complete conversion of the alkyl alcohol to form the corresponding dialkyl ether and water; recovering the dialkyl ether from the distillation column reactor as an overheads fraction; recovering the water from the distillation column reactor as a bottoms fraction.

15 Claims, 7 Drawing Sheets

METHOD FOR THE PRODUCTION OF DIMETHYL ETHER

BACKGROUND OF DISCLOSURE

1. Field of the Disclosure

Embodiments disclosed herein relate generally to the preparation of dimethyl ether by catalytic reaction of methanol with itself and the concurrent distillation and separation of the product and reactants. More particularity the invention relates to a process for producing essentially pure dimethyl ether and water.

2. Background

The preparation of ethers by the dehydration of alcohols using an acid is known, e.g.,

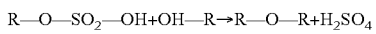

U.S. Pat. No. 3,267,156 discloses that acidic cation exchange resins effectively catalyze the selective dehydration of alcohols to ethers as exemplified by the production of diisopropyl ether.

U.S. Pat. No. 3,931,349 discloses a process to convert methanol to gasoline boiling components. In a first step, a methanol feed is vaporized and converted to a mixture of dimethyl ether, methanol, and water by contact with a catalyst, such as gamma alumina. The exothermic alcohol dehydration reaction increases the temperature of the resulting stream such that contact of the stream with a ZSM-5 zeolite results in the formation of gasoline boiling range aromatics. The dehydration reaction is indicated as releasing about 750 BTU per pound of methanol which may cause large temperature increases and may result in high catalyst aging rates.

U.S. Pat. No. 5,037,511 discloses a process to produce pure dimethyl ether by catalytic dehydration of methanol at a temperature of 140-500° C. and a pressure of 1-50 bar followed by distillation. The dehydration product is fed to a distillation column to separate the dimethyl ether from water, unreacted alcohol, and reaction byproducts where the dimethyl ether is withdrawn from the column at one or more trays that are at least one tray above the bottom of the column, characterized in that (a) liquid and/or gaseous fraction(s) containing reaction by-products are withdrawn at least 3 trays below the lowest tray from which pure dimethyl ether is withdrawn, and (b) the tray(s) from which pure dimethyl ether is withdrawn, is at least 8 trays above the highest feed tray.

U.S. Pat. No. 5,316,627 discloses a process for the production of odorless dimethyl ether. An alcohol dehydration product stream (i.e., a crude dimethyl ether stream), containing methanol, dimethyl ether, and water, is fed to a single distillation column where a dimethyl ether draw is subsequently treated with an insoluble acid ion exchange resin to remove impurities.

U.S. Pat. No. 5,684,213, incorporated herein by reference, discloses a process for the production of dialkyl ethers in a distillation column reactor in the presence of added hydrogen. While various ranges of conditions are disclosed for ether production, the conditions specifically disclosed for the production of dimethyl ether are pressures ranging up to 600 psig and a catalyst zone temperature of 350-400° C. (662-752° F.). Also disclosed is that the overhead product stream may be subsequently fractionated to result in 99.9+% pure dimethyl ether.

Although described as benefiting the process, addition of hydrogen to the distillation column reactor may add to the operating and capital costs of the process. For example, hydrogen may result in unwanted by-products, may require the use of compressors and higher pressure-rated equipment, and may result in increased piece count, among others. Additionally, each of the above-described processes describes the dehydration of alcohol to form a crude ether product stream which is subsequently separated to form a pure ether product.

Accordingly, there exists a need for a catalytic distillation process for the production of substantially pure dialkyl ethers which does not require the use of hydrogen. Additionally, there also exists a need for processes which may eliminate the need for downstream separation, treatment, or purification of the resulting dehydration reaction products.

SUMMARY OF THE DISCLOSURE

In one aspect, embodiments disclosed herein relate to a process for the production of dialkyl ether, the process including: feeding a stream comprising an alkyl alcohol to a distillation column reactor system; concurrently in the distillation column reactor system: i) contacting the alkyl alcohol with a catalytic distillation structure in a distillation reaction zone thereby catalytically reacting at least a portion of the alkyl alcohol to form a corresponding dialkyl ether and water; and ii) fractionating the resulting dialkyl ether from the water; operating the distillation column reactor system to obtain substantially complete conversion of the alkyl alcohol to form the corresponding dialkyl ether and water; recovering the dialkyl ether from the distillation column reactor as an overheads fraction; recovering the water from the distillation column reactor as a bottoms fraction.

Other aspects and advantages will be apparent from the following description and the appended claims.

DETAILED DESCRIPTION

Figure 2:
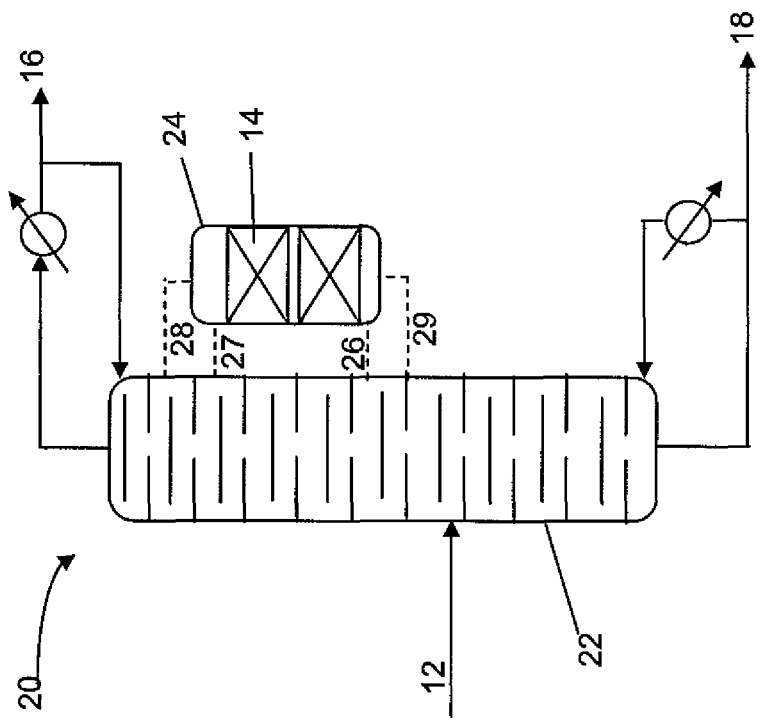
FIG. 2 is a simplified process flow diagram of a distillation column reactor system for the production of dialkyl ethers according to embodiments disclosed herein

In one aspect, embodiments disclosed herein relate to a process for the production of dialkyl ethers. More specifically, embodiments disclosed herein relate to a process for the production of dialkyl ethers from alkyl alcohols in a distillation column reactor system. In some embodiments, the distillation column reactor system may be operated such that substantially complete conversion of the alkyl alcohol.

Within the scope of this application, the expression "catalytic distillation reactor system" denotes an apparatus in which the alcohol condensation reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation processes may be preferred over conventional liquid phase reaction followed by separations, a catalytic distillation column reactor may have the advantages of decreased piece count, efficient heat removal heat of reaction may be absorbed into the heat of vaporization of the mixture), and a potential for shifting equilibrium.

Dialkyl ethers may be prepared by the dehydration of alcohols using an acid, such as sulfuric acid. For example, methanol may be dehydrated to form dimethyl ether, ethanol may be dehydrated to form diethyl ether, and a mixture of ethanol and methanol may for both dimethyl and diethyl ether as well as methyl ethyl ether, as follows:

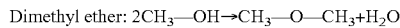
Dimethyl ether: $2CH_3—OH \rightarrow CH_3—O—CH_3+H_2O$

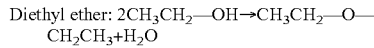
Diethyl ether: $2CH_3CH_2—OH \rightarrow CH_3CH_2—O—CH_2CH_3+H_2O$

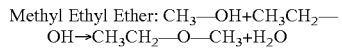
Methyl Ethyl Ether: $CH_3—OH+CH_3CH_2—OH \rightarrow CH_3CH_2—O—CH_3+H_2O$ Each of the above reactions may be catalyzed using an acid catalyst, such as sulfuric acid, or other catalysts as described below. Side reactions may include the formation of olefins, oligomers, aromatics, and coke, which typically cause fouling of the catalyst.

Other alcohols may also be used in embodiments disclosed herein. For example, propanol, isopropanol, n-butanol, 2-butanol, and isobutanol, among others, may also be used. Alcohols may also be used in admixture, such as with one of ethanol and methanol. Use of higher alcohols, such as propanol and butanol, may depend on selectivity of the catalyst to produce mixed ethers (e.g., methyl propyl ether), the concentration of the higher alcohol, the resulting boiling point of the dialkyl ether, and the potential for the reactants and/or products to form an azeotrope with water. For ease of separations, and to obtain substantially pure product streams, the boiling point of resulting ethers should be lower than the boiling point of water under column operating conditions.

Alkyl alcohol feeds may contain impurities, such as water. For example, alcohol produced from a syngas reaction may contain a certain amount of water. Typically, the water is removed from the alcohol. However, as water is a byproduct of the alcohol condensation reaction, alcohol feeds used in embodiments disclosed herein may include water as an impurity. Excessive water in the feed may decrease pre-reactor conversion equilibrium, discussed below, and may result in increased reboiler duties, but water as a feed impurity may be tolerated in systems described herein.

In some embodiments, alcohol feeds may include up to 40 weight percent water; up to 30 weight percent water in other embodiments; up to 20 weight percent water in other embodiments; up to 10 weight percent water in other embodiments; up to 5 weight percent water in other embodiments; and up to 2 weight percent water in yet other embodiments. In other embodiments, alcohol feeds may be substantially pure alcohol or alcohol mixtures.

As described above, alkyl alcohols may be fed to a distillation column reactor system, where the alcohols contact a catalyst and react to form dialkyl ethers and water. The dialkyl ether, boiling at a temperature lower than water, may be recovered as an overhead fraction. Water, boiling at a temperature greater than the dialkyl ether, may be recovered as a bottoms fraction.

In some embodiments, the distillation column reactor system may include a distillation column reactor. A distillation column reactor may include one or more distillation reaction zones, where a catalyst structure may also serve as a distillation structure, resulting in the concurrent reaction and fractionation of the reactants and products. Feed and distillation reaction zone location may depend upon the respective boiling points of the reactants and products.

Distillation reaction zones may also be located in a portion of a divided wall distillation column. Divided wall distillation columns are described in, for example, U.S. Pat. Nos. 4,230,533; 4,582,569; 4,826,574; 5,339,648, 5,755,933, and 7,026,517. Divided wall columns may include distillation vessels having a vertical partition separating one side from the other for a portion or all of the height of the vessel. The divided wall column may have a common rectification section, a common stripping section, or both. In some embodiments disclosed herein, the distillation column reactor may be a divided wall column, where the divided wall column comprises at least one catalytic reaction zone. In other embodiments, the feed may be to a non-catalytic distillation zone of the divided wall column.

In other embodiments, the distillation column reactor system may include a primary distillation column and a side reactor. Feed for the side reactor may include a side draw from the primary distillation column, and a product stream may be returned to the primary distillation column. Side draw and return locations may depend on the respective boiling points of the reactants and products. In some embodiments, the side reactor may include a fixed bed reactor; in other embodiments, the side reactor may include a distillation column reactor, having both vapor and liquid feed and return to the primary distillation column.

In various embodiments, heat transfer systems may be used to integrate the heating and cooling of the feed and product streams. For example, the alkyl alcohol feed may be heated using at least a portion of the overhead stream, at least a portion of the bottoms stream, or a combination thereof. Other heat integration configurations may also be used.

In other embodiments, a pre-reactor may be used to convert at least a portion of the alkyl alcohol feed to dialkyl ether. For example, a fixed bed reactor may be used to convert the alkyl alcohol to dialkyl ether, where the fixed bed reactor may include upflow, downflow, or other flow configurations. The fixed bed reactor may be operated liquid continuous, or may be operated at a boiling point of the reaction mixture, such as in a down flow boiling point reactor or a pulse flow reactor. Operating conditions in the fixed bed reactor may be selected to achieve partial conversion of the alkyl alcohol, such as at least 25 weight percent of the alkyl alcohol; at least 50 weight percent in other embodiments.

In yet other embodiments, operating conditions in the fixed bed reactor may be selected to achieve reaction equilibrium. For example, methanol dehydration to dimethyl ether may have a thermodynamic equilibrium limitation of approximately 80-87 weight percent conversion of the alcohol. The resulting mixture may then be fed to the distillation column reactor system.

Due to the concurrent fractionation and separation of reactants and products, essentially complete conversion of the alkyl alcohol may be obtained in the distillation column reactor system. The success of the catalytic distillation approach lies in an understanding of the principles associated with distillation. Because the reaction is occurring concurrently with distillation, the initial reaction product, the dialkyl ether, is removed from the reaction zone nearly as quickly as it is formed. This removal of the dialkyl ether minimizes decomposition of the ether, which may be catalyzed by the same catalyst. Additionally, the reaction has an increased driving force because the reaction products have been removed and cannot contribute to the reverse reaction (Le Chatelier's Principle).

The inventors have surprisingly found that distillation column reactor system operating conditions may be maintained such that substantially complete conversion of the alkyl alcohol may be obtained. Substantially complete conversion, as used herein, refers to the conversion of at least 98 weight percent of the reactants (alkyl alcohols) to form products, including any byproducts. In other embodiments, at least 98.5 weight percent of the alkyl alcohol may be obtained; at least 99 weight percent in other embodiments; at least 99.5 weight percent in other embodiments; at least 99.8 weight percent in other embodiments; and at least 99.9 weight percent in yet other embodiments.

The dialkyl ether may be recovered as an overheads fraction, which may be essentially pure dialkyl ether in some embodiments. Water, formed during the condensation reaction, may be recovered as a bottoms fraction, which may be essentially pure water in some embodiments. Essentially pure, as used herein, refers to a composition or mixture, such as the bottoms fraction or overheads fraction, containing at least 98 weight percent of the indicated compound, such as the dialkyl ether or the water. In other embodiments, the recovered fractions may contain at least 98.5 weight percent of the indicated compound; at least 99 weight percent in other embodiments; at least 99.5 weight percent in other embodiments; at least 99.8 weight percent in other embodiments; and at least 99.9 weight percent in yet other embodiments.

Side reaction products, as mentioned above, typically foul the catalyst. However, minor amounts of higher boiling materials may be washed down the column and exit with the bottoms fraction. Any light components formed, such as light olefins ($C_{2-4}$ olefins) may exit the distillation column reactor system with the overheads fraction. These are typically minority components and do not significantly affect the purity of the product streams.

Figure 1:
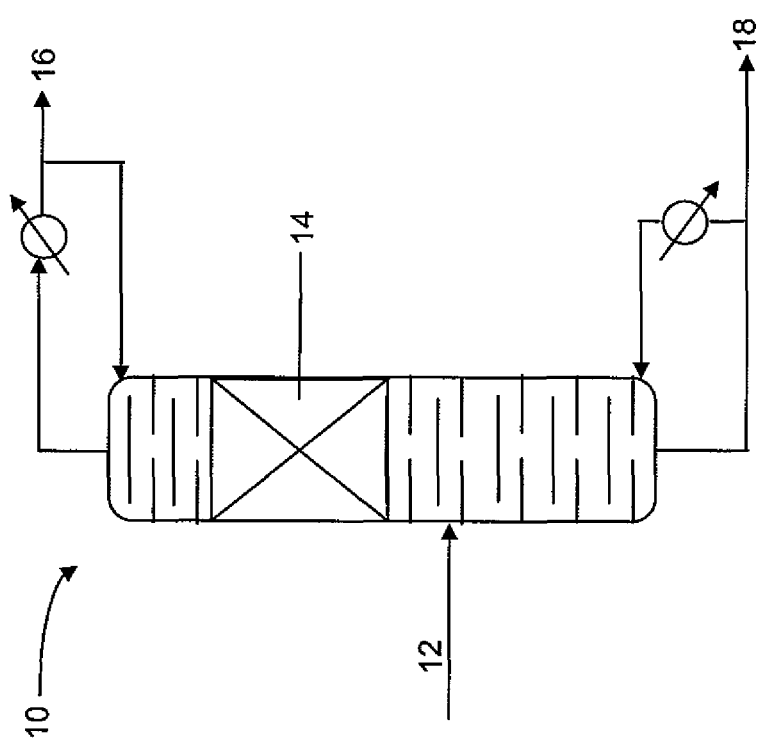
FIG. 1 is a simplified process flow diagram of a distillation column reactor system for the production of dialkyl ethers according to embodiments disclosed herein

Referring now to FIG. 1, a simplified process flow diagram of a distillation column reactor system for the production of dialkyl ethers according to embodiments disclosed herein is illustrated. One skilled in the art would recognize that, although not depicted, pumps, valves, vessels, storage tanks, and other equipment commonly used for the processes described and illustrated herein are not shown so as to simplify the diagram.

Alkyl alcohol may be fed to a distillation column reactor system 10 via conduit 12. The feed location on distillation column reactor system 10 may be above, below, or within distillation reaction zone 14 containing a dehydration catalyst for converting the alkyl alcohol to a corresponding dialkyl ether and water. While the reaction is proceeding, the reaction products are concurrently fractionated, allowing dialkyl ether to be recovered as an overheads fraction 16 and water to be recovered as a bottoms fraction 18.

Operating conditions, such as feed temperature, overheads temperature, bottoms temperature, the temperature profile of the column, feed rate, reflux ratio, and other operating variables may be selected to obtain substantially complete conversion of the alkyl alcohol to the corresponding dialkyl ether and water. In some embodiments, operating the distillation column reactor system may include maintaining a temperature profile across the distillation reaction zone to satisfy the kinetics of the dehydration. In other embodiments, operating the distillation column reactor to obtain substantially complete conversion of the alkyl alcohol may include maintaining a reflux rate above the reaction zone sufficient to separate the dimethyl ether from the unreacted alcohol.

In yet other embodiments, the operating conditions may be selected such that the alkyl alcohol is essentially deadheaded in the column. The temperature of the overhead fraction or upper column tray(s) may be sufficiently below the boiling point of the alkyl alcohol, and the temperature of the bottom tray(s) may be sufficiently above the boiling point of the alkyl alcohol such that the alcohol remains in the column until reacted. In this manner, essentially pure dialkyl ether may be recovered as an overheads fraction, and essentially pure water may be recovered as a bottoms fraction.

Referring now to FIG. 2, a simplified process flow diagram of a distillation column reactor system 20 for the production of dialkyl ethers according to other embodiments disclosed herein is illustrated, where like numerals represent like parts. Alkyl alcohol may be fed to distillation column reactor system 20 via conduit 12. Distillation column reactor system 20 may include a distillation column 22 and a side reactor 24. The feed location on distillation column reactor system 20 may be above, below, or between the draw and return locations for the side reactor containing a reaction zone 14 containing a dehydration catalyst for converting the alkyl alcohol to a corresponding dialkyl ether and water.

In some embodiments, side reactor 24 may include a downflow fixed bed reactor, including a liquid draw and a liquid or mixed vapor/liquid return. In other embodiments, side reactor 24 may include a catalytic distillation reactor, including both vapor draw 26 and liquid draw 27 and vapor return 28 and liquid return 29. While the reaction is proceeding, the reaction products are concurrently fractionated, allowing dialkyl ether to be recovered as an overheads fraction 16 and water to be recovered as a bottoms fraction 18.

Figure 3:
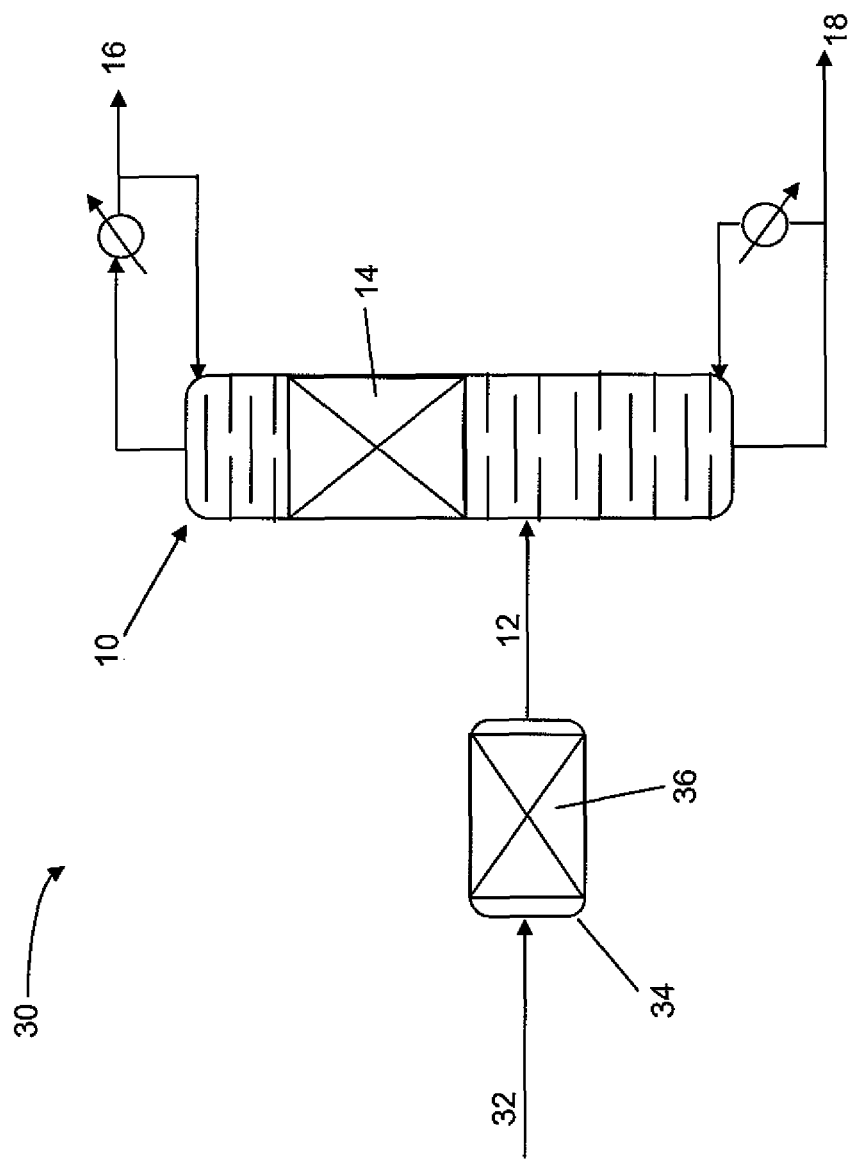
FIG. 3 is a simplified process flow diagram of a process for the production of dialkyl ethers according to embodiments disclosed herein is illustrated

Referring now to FIG. 3, a simplified process flow diagram of a process 30 for the production of dialkyl ethers according to other embodiments disclosed herein is illustrated. Alkyl alcohol may be fed via conduit 32 to a fixed bed reactor 34 having a reaction zone 36 containing a dehydration catalyst zone for converting at least a portion of the alkyl alcohol to a corresponding dialkyl ether and water. Effluent from fixed bed reactor 34 may be forwarded via conduit 12 to a catalytic distillation reaction system, such as those described above or illustrated in FIGS. 1 and 2. As illustrated in FIG. 3, the partially converted alkyl alcohol stream may be fed to a distillation column reactor system 10 via conduit 12. The feed location on distillation column reactor system 10 may be above, below, or within distillation reaction zone 14 containing a dehydration catalyst for converting the alkyl alcohol to a corresponding dialkyl ether and water. While the reaction is proceeding, the reaction products are concurrently fractionated, allowing dialkyl ether to be recovered as an overheads fraction 16 and water to be recovered as a bottoms fraction 18.

Catalysts

Catalysts that may be used in the pre-reactor and the distillation column reactor system are dehydration catalysts, usually characterized as acidic dehydration catalysts. Zeolites and metal substituted cationic resin catalysts may be used for this reaction, but other mildly acidic catalyst may also be used.

Naturally occurring zeolites have irregular pore size and are not generally considered as equivalent to synthetic zeolites. In some embodiments, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Synthetic zeolites may be prepared in the sodium form, that is, with a sodium cation in close proximity to each aluminum tetrahedron and balancing its charge. A number of principal types of molecular sieves have been reported, such as A, X, Y, L, erionite, omega, beta, and mordenite. The A-type molecular sieves have relatively small pore size. By the term pore size is meant the effective pore size (diameter) rather than the free pore size (diameter). X- and Y-type molecular sieves generally have a larger pore size (approximately 7.4 Å) and differ as to the range of ratio of $Al_2O_3$ to $SiO_2$. Type L and other types listed have still higher ratios of SiO, to $Al_2O_3$, as known in the art.

Zeolite catalysts that may be used in embodiments disclosed herein are the acid form of the zeolite or at least exhibit acidic characteristics. The acid form is commercially available, but also may be prepared by treating the zeolites with acid to exchange Na for hydrogen. Another method to produce the acid form is to treat the zeolite with decomposable cations (generally ammonium ions) to replace Na with the decomposable ions and thereafter to heat the mole sieve to decompose the cation leaving the acid form. Generally the Na form is treated with ammonium hydroxide to remove the Na and thereafter the zeolite is heated to a temperature of about 350° C. to remove the ammonia. The removal of $Na^+$ ions with $NH_4^+$ is more easily carried out than with multivalent ions, as described below, and these catalysts are generally more active, but less stable to heat than the multivalent cation exchange forms. Zeolites, which have had their alkali metal reduced to low levels by partial treatment with $NH_4^+$ and partial multivalent metal cation exchange, may be expected to possess increased activity and increased stability.

Pore size within the crystal lattice may be significant in this reaction. According to one theory of molecular sieve catalytic activity, zeolite catalysis occurs primarily: inside the uniform crystal cavities, consequently: zeolitic catalyst activity depends on the number of aluminum atoms in the crystal and thus on the chemical composition of the crystal. Moreover, these catalytic sites are fixed within the rigid structure of the crystal, meaning that access to active sites can be altered by altering the structure of the crystal.

In some embodiments, resin catalysts may be used. For example, resin catalyst compositions such as sulfonic acid resins which have at least 50% of the sulfonic acid groups neutralized with one or more metal ions of Groups 4-12 of the Periodic Table, the rare earth metals, or mixtures thereof. The balance of the sulfonic acid groups may be neutralized with an alkali metal or alkaline earth metal, ammonium, or mixtures thereof. The sulfonic acid may be attached to any polymeric backbone. In some embodiments, the metal ions may include one or more of Ti, V, Cr, Mn, Fe, Co, Ni, Cu, Zn, Zr, Nb, Mo, Ru, Rh, Pd, Ag, Cd, Ta, W, Re, Pt, Ce, Nd, Sm, and Eu. The metal modified resin catalyst compositions are disclosed in U.S. Pat. Nos. 4,551,567 and 4,629,710, each of which are incorporated herein.

The acid cation exchange resins are well known and have a wide variety of uses. The resins are cation exchangers that contain sulfonic acid groups which may be obtained by polymerization or copolymerization of aromatic vinyl compounds followed by sulfonation. Aromatic vinyl compounds suitable for preparing polymers or copolymers are: styrene, vinyl toluene, vinyl naphthalene, vinyl ethylbenzene, methyl styrene, vinyl chlorobenzene, and vinyl xylene. A large variety of methods may be used for preparing these polymers. For example, polymerization alone or in admixture with other monovinyl compounds, or by crosslinking with polyvinyl compounds, such as divinyl benzene, divinyl toluene, and divinylphenylether, among others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products may contain an average of 1.3 to 1.8 sulfonic acid groups per aromatic nucleus. Particularly, suitable polymers containing sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, DE 908,247).

The ion exchange resin may have a granular size of about 0.25 to 1 mm, although particles from 0.15 mm up to about 2 mm may be used. The finer catalysts provide high surface area, but also result in high pressure drops through the reactor. The macroreticular form of these catalysts have a much larger surface area exposed and undergo limited swelling in a non-aqueous hydrocarbon medium compared to the gelular catalysts.

The metal modified catalyst may be prepared by contacting a macroporous matrix containing a sulfonic acid group with an aqueous solution of metal salts and solutions of alkali metal salts, alkaline earth metal salts, and/or ammonium salts to neutralize the acid groups. An alternative procedure for the preparation of the metal modified cation resin catalyst compositions comprises contacting a sulfonic acid cation exchange resin, e.g., a macroporous matrix of a polyvinyl aromatic compound crosslinked with a divinyl compound and having thereon from about 3 to 5 milli-equivalents of sulfonic acid groups per gram of dry resin, (1) with an aqueous solution of a soluble metal salt as described above, such as Al, Fe, Zn, Cu, Ni, or mixtures thereof, to neutralize at least 50% to less than 100% of the available sulfonic acid groups with metal ions to produce a partially neutralized resin, and (2) thereafter contacting the partially neutralized resin with an aqueous solution containing a soluble compound of an alkali or alkaline earth metal of Groups 1 or 2, of the Periodic Table, or mixture thereof to neutralize the remaining sulfonic acid groups. In the final alkali neutralization step under the alternate procedure, care must be exercised to not contact the partially neutralized resin with a large excess of alkali or alkaline earth metal ions, (a slight excess, up to about 20%, beyond that required to neutralize the residual sulfonic acid groups may be used) since they appear to form double salts or possibly elute the metal ions, which may reduce the activity of the catalyst.

Resin catalyst composition useful herein may be characterized as a solid comprising a macroporous matrix of polyvinyl aromatic compound crosslinked with a divinyl compound and having thereon from about 3 to 5 milli-equivalents of sulfonic acid groups per gram of dry resin, wherein at least 50 percent to less than 100 percent of said sulfonic acid groups are neutralized with a metal ion as described above; in other embodiments, at least 59 percent may be neutralized; and from about 70 percent to about 90 percent neutralized in yet other embodiments. Sulfonic acid groups not neutralized with the metal ion may be neutralized with alkali or alkaline earth metal ions of Group 1 or 2 of the Periodic Table, ammonium ions, or mixtures thereof.

The particulate catalyst may be employed by enclosing them in a porous container such as cloth, screen wire, or polymeric mesh. The material used to make the container may be inert to the reactants and conditions in the reaction system. Particles of about 0.1 5 mm size or powders up to about ¼ inch diameter may be disposed in the containers. The container used to hold the catalyst particles may have any configuration, such as the pockets disclosed in the commonly assigned patents noted above, or the container may be a single cylinder, sphere, doughnut, cube, tube, or the like.

It is not essential that the spacing component entirely covers the catalyst component. It is only necessary that the spacing component intimately associated with the catalyst component act to space the various catalyst components away from one another as described above. Thus, the spacing component provides in effect a matrix of substantially open space in which the catalyst components are randomly but substantially evenly distributed. One such structure is that shown in U.S. Pat. No. 5,730,843, incorporated by reference herein. In addition, commonly assigned U.S. Pat. Nos. 4,443,559, 5,057,468, 5,262,012, 5,266,546, and 5,348,710 disclose a variety of catalyst structures for this use and are incorporated by reference herein.

U.S. Pat. No. 6,740,783, incorporated by reference herein, discloses other catalyst useful for the production of dialkyl ethers from alcohol, including crude alcohols containing some water Disclosed are hydrophobic zeolites serving as a catalyst, such as USY, mordenite, ZSM-type, and Beta zeolites whose hydrogen cations are partially replaced with suitable metal ions, such as Group 1, 2, 11, or 12 metal ions, or ammonium ions. Other useful catalysts for the dehydration reaction are disclosed in U.S. Pat. No. 3,931,349.

Catalysts used in the fixed bed reactor in various embodiments disclosed herein may include metal-treated zeolites, either acidic or basic, hydrofluoric acid-treated clays, and silica-alumina catalysts, such as a 20% silica-alumina, among the other catalysts described above. Catalysts used in the distillation column reaction zone may include metalized resins and silica-alumina catalysts, among the other catalysts described above. Metalized resin catalysts may include such catalysts as zinc-treated AMBERLYST 15 and copper-treated AMBERLYST 35, among others.

Pre-Reactor and Distillation Column Reactor Operating Conditions

Operating conditions in the pre-reactor and the distillation column reactor may depend upon the purity of the methanol feed and the types of catalyst used in the pre-reactor (if present) and the distillation column reactor system, among other variables. Typical reaction zone operating conditions include temperatures ranging from 120° C. to 500° C. and pressures ranging from 1 to 50 bar.

In some embodiments, pre-reactor temperatures may range from about 100° C. to about 300° C. (about 212 to about 572° F.). In other embodiments, pre-reactor temperatures may range from about 120° C. to about 260° C. (about 248 to about 500° F.); from about 150° C. to about 200° C. (about 302 to about 392° F.) in other embodiments; and from about 170° C. to about 180° C. (about 338 to about 356° F.), such as about 175° C. (about 347° F.), in yet other embodiments.

In some embodiments, pre-reactor pressures may range from about 3 bar to about 200 bar (absolute). In other embodiments, pre-reactor pressures may range from about 5 bar to about 100 bar; from about 10 bar to about 50 bar in other embodiments; from about 15 bar to about 45 bar in other embodiments; and from about 20 to about 30 bar, such as about 25 bar, in yet other embodiments.

In some embodiments, a distillation column reactor system may include a distillation reaction zone having temperatures in the range from about 50° C. to about 300° C. (about 122 to about 572° F.). In other embodiments, pre-reactor temperatures may range from about 100° C. to about 260° C. (about 212 to about 500° F.); from about 150° C. to about 200° C. in other embodiments (about 302 to about 392° F.); and from about 170° C. to about 180° C. (about 338 to about 356° F.), such as about 175° C. (about 347° F.), in yet other embodiments.

In some embodiments, a distillation column reactor system may include a distillation reaction zone having a pressure in the range from about 1 bar to about 300 bar (absolute). In other embodiments, pre-reactor pressures may range from about 2 bar to about 200 bar; from about 5 bar to about 100 bar in other embodiments; from about 10 bar to about 50 bar in yet other embodiments; and from about 10 bar to about 30 bar, such as about 20 bar, in yet other embodiments.

The temperature profile across the distillation column reaction zone should be sufficient to satisfy the kinetics of the alcohol dehydration reaction. The temperature profile should also be sufficient to obtain substantially complete conversion of the alkyl alcohol. For example, for a catalyst having high activity, temperatures and pressures may be less severe than for a catalyst having a lower activity, where conditions for each may be selected to satisfy the kinetics of the dehydration reaction and to obtain substantially complete conversion of the alkyl alcohol.

The severity of operating conditions in the pre-reactor may also depend upon the amount of alcohol conversion required. The amount of alcohol conversion required may also affect the choice of catalyst used in the pre-reactor. For example, a desired pre-reactor conversion of 20 weight percent may require less severe operating conditions and/or a lower activity catalyst than for a pre-reactor conversion approaching equilibrium, 80 to 87 weight percent conversion.

The choice of catalyst and the severity of operating conditions in the distillation column reaction system may also be affected by the amount of alcohol conversion required. For example, the catalyst choice and conditions may be different for a pre-reactor conversion of about 20 weight percent as compared to a pre-reactor conversion approaching equilibrium.

Accordingly, the catalysts used in the distillation column reactor system may be the same or different than that used in the pre-reactor, when present. In some embodiments, it may be preferred to use a lower activity catalyst in the distillation column reactor system, thus allowing for extended catalyst life. The catalyst used in the pre-reactor may be of a higher activity, such as where pre-reactors are run in parallel, allowing for one to be repacked or regenerated while the other is operational.

Distillation column operating conditions may also depend upon the activity of the catalyst. For example, the amount of alcohol converted to dialkyl ether per distillation reaction stage may vary from 5 weight percent to 50 weight percent or more. Distillation column operating conditions, such as temperatures, pressures, and reflux ratios may need to be adjusted to obtain substantially complete conversion of the alkyl alcohol. In some embodiments, reflux ratios may vary from about 0.1 or 0.5 to about 10; from about 0.5 to about 5 in other embodiments; from 0.6 to 3 in other embodiments; from 0.7 to 2.5 in other embodiments; and from 0.9 to 2 in yet other embodiments. In relation to alcohol conversion per distillation reaction stage, it has been found that higher reflux ratios are required at lower conversion per stage. For example, for an alcohol conversion per stage of approximately 20 weight percent, the reflux ratio may range from 2 to 3 to obtain complete conversion of the alcohol, such as a reflux ratio of about 2.4 in some embodiments. Comparatively, for an alcohol conversion per stage of approximately 40 weight percent, the reflux ratio may range from 0.5 to 2 to obtain complete conversion of the alcohol, such as a reflux ratio ranging from 1 to 1.6 in some embodiments.

Although embodiments of processes disclosed herein may result in the production of substantially pure dialkyl ether and water product streams, these streams may also undergo subsequent treatment. The need for subsequent treatment may depend upon the quality of the alcohol feed or the reaction byproducts. Subsequent treatment of the product streams may include, for example, treatment of the dialkyl ether stream with an acidic ion exchanger to remove odor-producing impurities. Other treatments may include the removal of heavier organic reaction byproducts from the water stream.

EXAMPLES

Example 1

Figure 4:
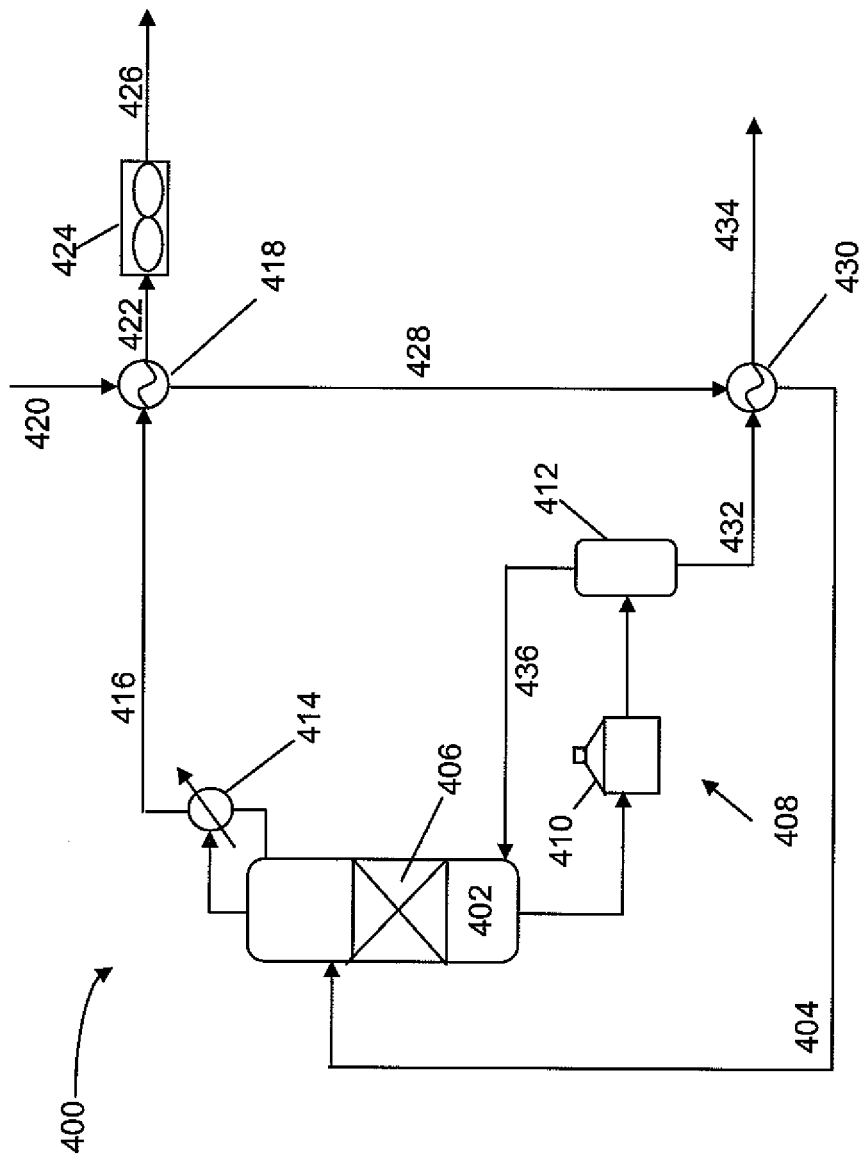
FIG. 4 is simplified process flow diagram of a process for the production of dialkyl ethers according to embodiments disclosed herein is illustrated

Methanol is reacted to form dimethyl ether in a distillation column reactor system 400 similar to that shown in FIG. 4. Preheated methanol feed is transmitted to distillation column reactor system 402 through feed conduit 404. Distillation column reactor system 402 includes trays and/or packing (not shown) and at least one catalytic distillation zone 406. Catalytic distillation zone 406 includes an alcohol condensation metalized resin catalyst (such as copper treated AMBERLYST 35) that results in approximately 40 percent conversion of the methanol to dimethyl ether per stage. Reboiler system 408, including heater 410 and drum 412, and overhead system 414 provide for vapor and liquid traffic through the column.

A substantially pure dimethyl ether fraction is recovered in overhead stream 416, and is fed to heat exchanger 418 to preheat the methanol feed in stream 420. The resulting overhead fraction in stream 422 is further cooled in heat exchanger 424 and recovered in stream 426. The resulting methanol stream 428 is further preheated in heat exchanger 430 recovering heat from a bottoms fraction recovered from drum 412 in stream 432, resulting in a cooled bottoms fraction recovered in stream 434 and preheated methanol stream 404. Vapor from drum 412 is returned to distillation column reactor 402 via conduit 436.

Temperatures and pressures in the reboiler system 408, including heater 410 and drum 412, and in the overhead system 414 are selected to obtain a desired temperature profile in distillation column reactor 402, resulting in essentially complete conversion of the methanol to dialkyl ether.

Figure 5:
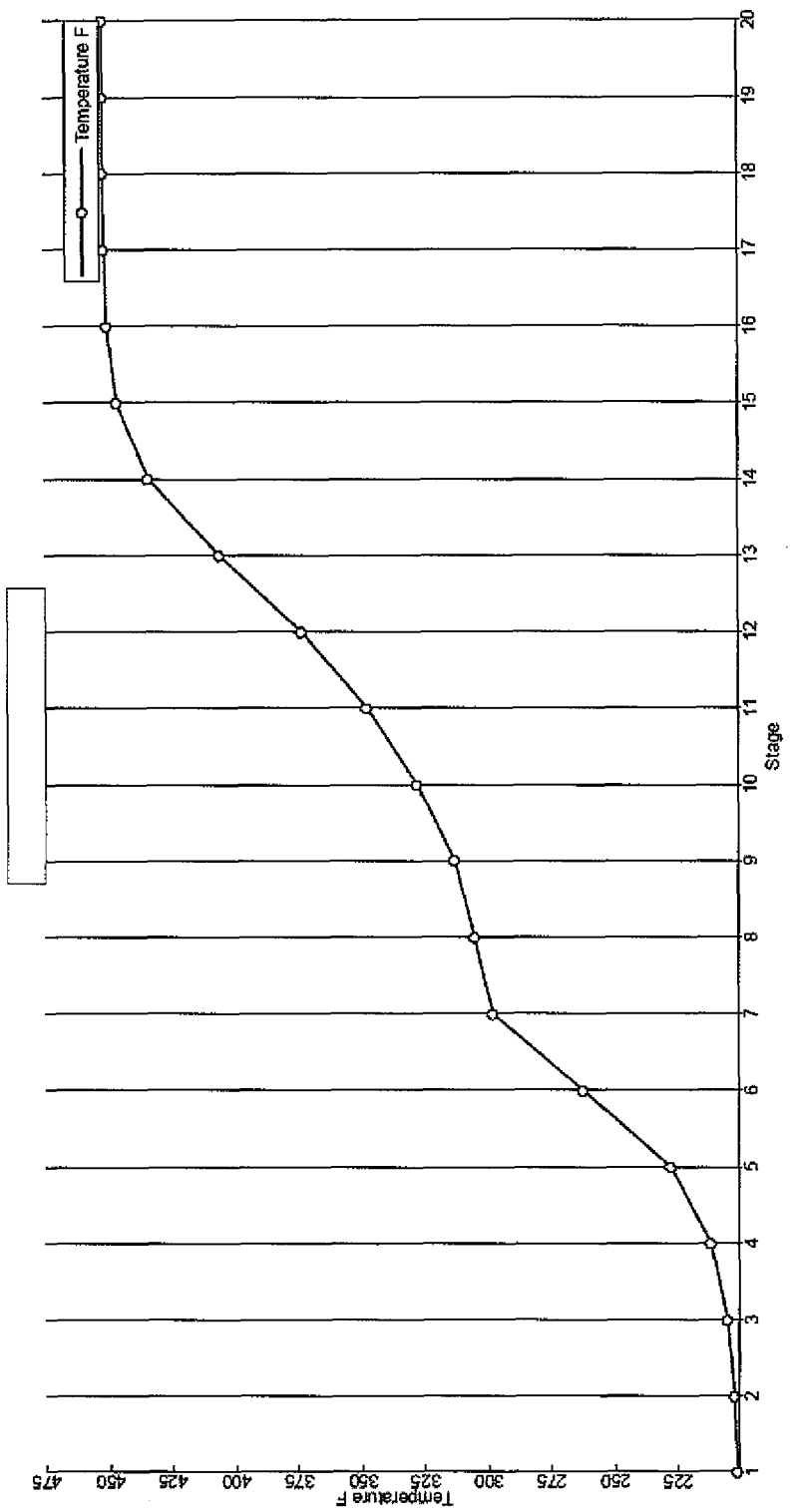
FIG. 5 illustrates a column temperature profile that may be used in a process for the production of dialkyl ethers according to embodiments disclosed herein.

In this example, conditions in distillation column reactor 402 are selected to give a temperature profile as shown in FIG. 5. Distillation column reactor 402 has 18 stages, excluding condenser 414 and reboiler system 408. The top tray in the column is at a temperature of about 202° F. and the bottom tray temperature is about 452° F. Pressure at the top of the column is approximately 425 psig and pressure drop across the column is about 5 psi. Preheated methanol feed enters distillation column reactor 402 at stage 6, and catalytic distillation reaction zone 406 is located from stages 9 through 14. The column reflux ratio is approximately 1.6. Feed stream compositions and conditions, as well as the resulting product streams and conditions are shown in Table 1.

TABLE 1

| | Stream No. | | | | | | | | |
|---|---|---|---|---|---|---|---|---|---|
| | 420 | 428 | 404 | 436 | 432 | 434 | 416 | 422 | 426 |
| Temperature, °C. (°F.) | 37.8 (100) | 87.8 (190) | 138.1 (280.6) | 233.3 (451.9) | 233.3 (451.9) | 93.3 (200) | 94.2 (201.5) | 93.3 (200) | 37.8 (100) |
| Pressure, barg (psig) | 27.2 (395) | 29.6 (430) | 29.3 (425) | 29.6 (430) | 29.6 (430) | 29.3 (425) | 29.3 (425) | 29.0 (420) | 26.5 (385) |
| Total Mass Flow Rate, kg/h (lb/h) | 289497.2 (638232) | 289497.2 (638232) | 289497.2 (638232) | 59453.2 (131071.9) | 81298.3 (179232) | 81298.3 (179232) | 208198.9 (459000) | 208198.9 (459000) | 208198.9 (459000) |
| Water, kg/h (lb/h) | 0 (0) | 0 (0) | 0 (0) | 59408.2 (130972.6) | 81289.8 (179213.4) | 81289.8 (179213.4) | 0 (0) | 0 (0) | 0 (0) |
| Methanol, kg/h (lb/h) | 289497.2 (638232) | 289497.2 (638232) | 289497.2 (638232) | 1.95 (4.3) | 0.36 (0.8) | 0.36 (0.8) | 331.0 (729.8) | 331.0 (729.8) | 331.0 (729.8) |
| Dimethyl ether kg/h, (lb/h) | 0 (0) | 0 (0) | 0 (0) | 43.1 (95.0) | 8.1 (17.8) | 8.1 (17.8) | 207867.9 (458270.2) | 207867.9 (458270.2) | 207867.9 (458270.2) |
| Mass Fraction | | | | | | | | | |
| Water | 0 | 0 | 0 | 0.999 | ~1 | ~1 | 0 | 0 | 0 |
| Methanol | 1 | 1 | 1 | trace | trace | Trace | 0.002 | 0.002 | 0.002 |
| Dimethyl Ether | 0 | 0 | 0 | 0.001 | Trace | Trace | 0.998 | 0.998 | 0.998 |

Operation of distillation column reactor 402 as described above results in substantially complete conversion of the methanol and the recovery of an essentially pure overhead dimethyl ether fraction 426 and an essentially pure bottoms water fraction 434, as shown in Table 1. Operating conditions are selected to result in the methanol feed being essentially trapped in the column, the overheads being at a temperature less than the boiling point of methanol, and the bottoms being at a temperature greater than the boiling point of methanol. By weight, approximately 99.9 percent conversion of the methanol is obtained and essentially pure dimethyl ether and water fractions are recovered in the overhead and bottoms streams, 426 and 434, respectively. Although not shown, additional heat exchangers may also be used to further cool overhead fraction 426 and bottoms fraction 434.

Example 2

Figure 6:
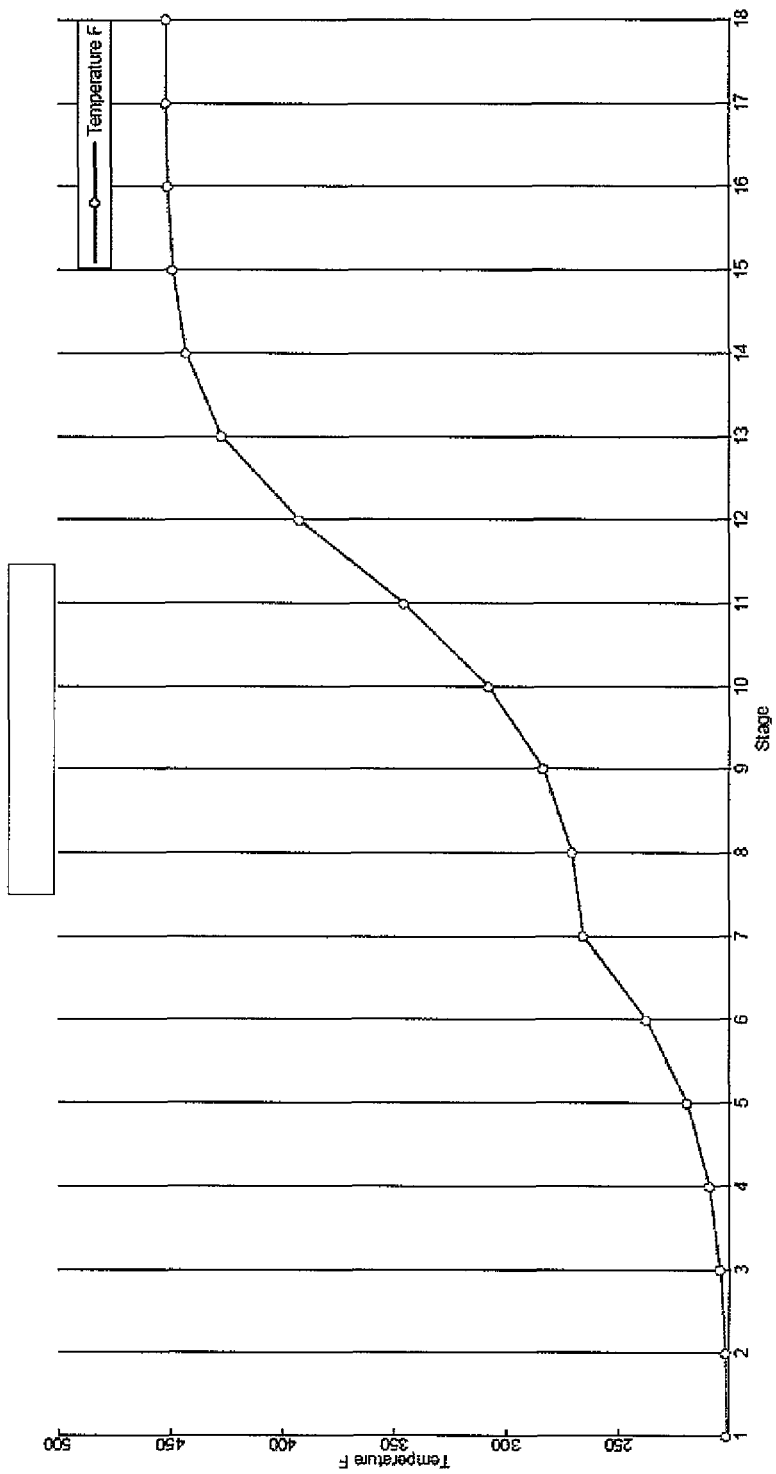
FIG. 6 illustrates a column temperature profile that may be used in a process for the production of dialkyl ethers according to embodiments disclosed herein.

A distillation column reactor system, similar to that described above in Example 1 in relation to FIG. 4, is used to convert methanol to dimethyl ether. Catalytic distillation zone 406 includes an alcohol condensation catalyst (such as 20% silica-alumina or metal-treated beta-zeolite) that results in approximately 20 percent conversion of the methanol to dimethyl ether per stage. By weight, approximately 99.9 percent conversion of the methanol is obtained with a reflux ratio of approximately 2.4 and a temperature profile as shown in FIG. 6. Essentially pure dimethyl ether and water fractions are recovered in the overhead and bottoms streams, 426 and 434, respectively.

Example 3

Figure 7:
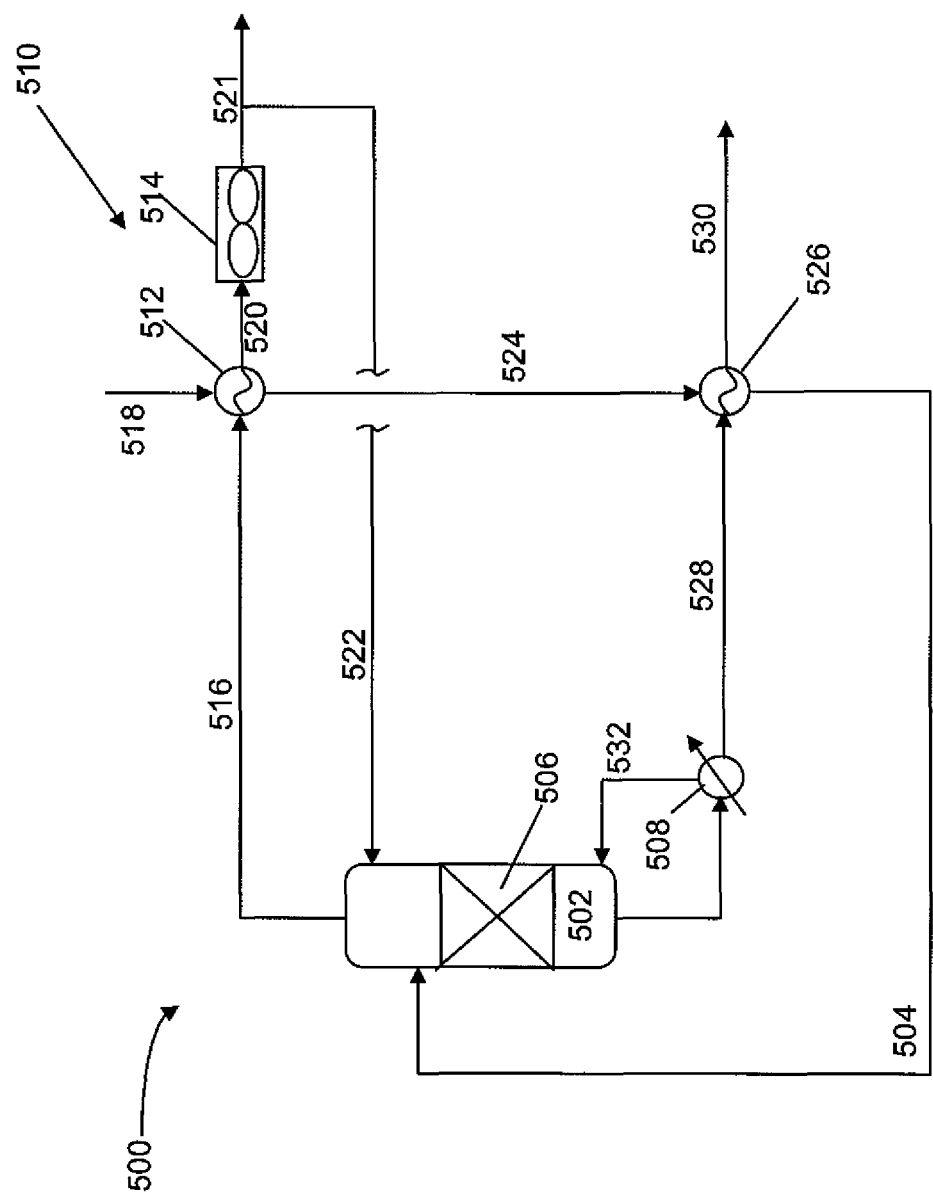
FIG. 7 is a simplified process flow diagram of a process for the production of dialkyl ethers according to embodiments disclosed herein is illustrated

Methanol is reacted to form dimethyl ether in a distillation column reactor system 500 similar to that shown in FIG. 7. Preheated methanol feed is transmitted to distillation column reactor system 502 through feed conduit 504. Distillation column reactor system 502 includes trays and/or packing (not shown) and at least one catalytic distillation zone 506. Catalytic distillation zone 506 includes an alcohol condensation catalyst (such as zinc-treated AMBERLYST 15) that results in approximately 40 percent conversion of the methanol to dimethyl ether per stage. Reboiler system 508 and overhead system 510, including heat exchanger 512 and primary condenser 514, provide for vapor and liquid traffic through the column.

A substantially pure dimethyl ether fraction is recovered in overhead stream 516, and is fed to heat exchanger 512 to preheat the methanol feed in stream 518. The resulting overhead fraction in stream 520 is further cooled in primary condenser 514 and recovered in stream 521, a portion of which is fed as column reflux in stream 522. The resulting methanol stream 524 is further preheated in heat exchanger 526, recovering heat from a bottoms fraction recovered from reboiler 508 in stream 528, resulting in a cooled bottoms fraction recovered in stream 530 and preheated methanol stream 504. Vapor from reboiler 508 is returned to distillation column reactor 502 via conduit 532.

Temperatures and pressures in the reboiler system 508 and the overhead system 510 are selected to obtain a desired temperature profile in distillation column reactor 502, resulting in essentially complete conversion of the methanol to dialkyl ether. In this example, conditions in distillation column reactor 502 are selected to give a temperature profile as shown in FIG. 8.

Figure 8:
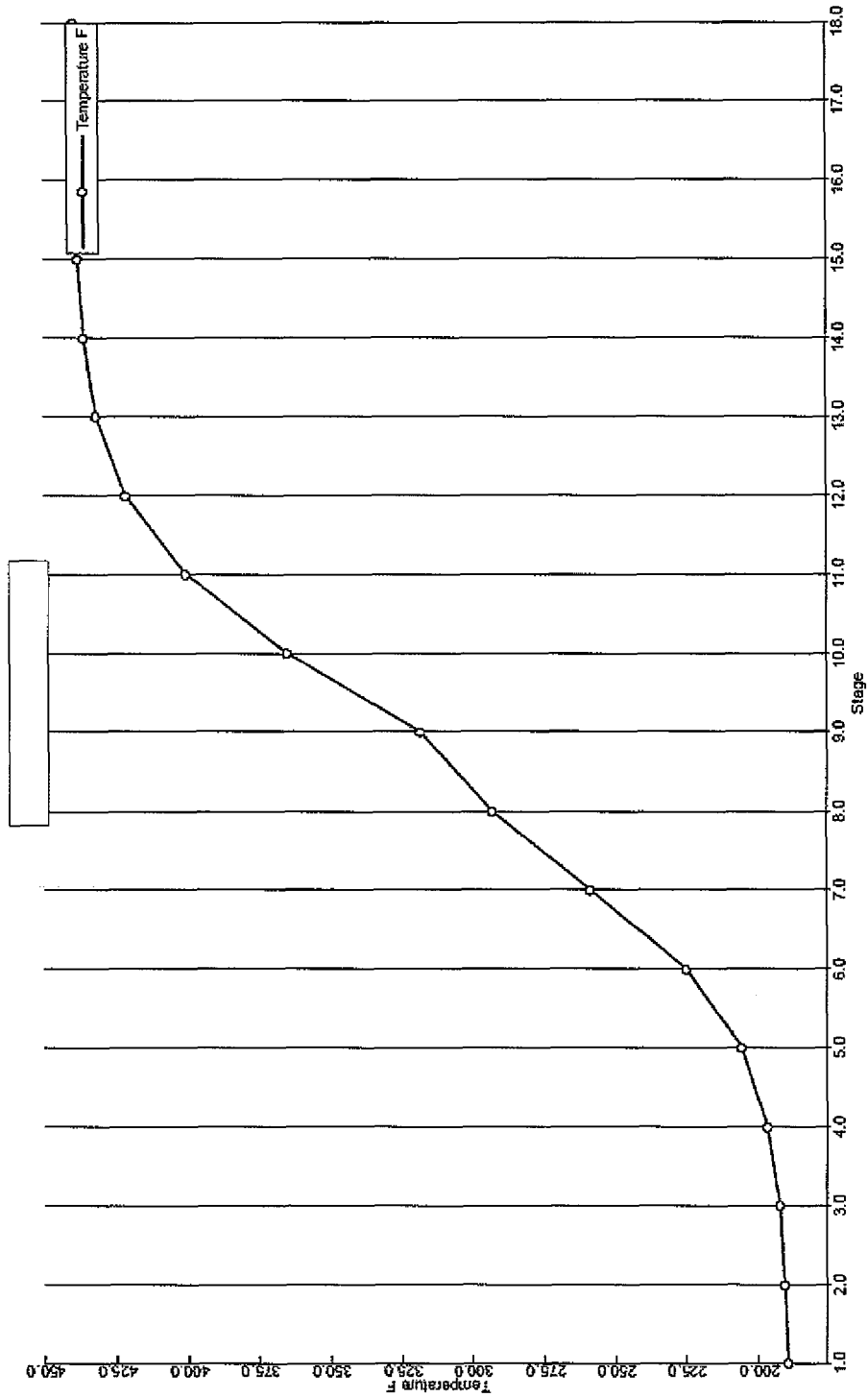
FIG. 8 illustrates a column temperature profile that may be used in a process for the production of dialkyl ethers according to embodiments disclosed herein.

As can be seen in FIG. 8, distillation column reactor 502 has 18 stages, excluding overhead system 510 and reboiler system 508. The top tray in the column is at a temperature of about 190° F. and the bottom tray temperature is about 440° F. Pressure at the top of the column is approximately 375 psig and pressure drop across the column is about 5 psi. Preheated methanol feed enters distillation column reactor 502 at stage 6, and catalytic distillation reaction zone 506 is located from stages 9 through 14. The column reflux ratio was approximately 1. Feed stream compositions and conditions, as well as the resulting product streams and conditions are shown in Table 2.

TABLE 2

| | Stream No. | | | | | | | | |
|---|---|---|---|---|---|---|---|---|---|
| | 518 | 524 | 504 | 528 | 530 | 516 | 520 | 522 | 521 |
| Temperature, °C. (°F.) | 39 (102.2) | 86.6 (187.9) | 135.8 (276.5) | 226.6 (439.8) | 88.3 (190.9) | 87.7 (189.8) | 87.5 (189.5) | 65.6 (150) | 65.6 (150) |
| Pressure, barg (psig) | 26.5 (385) | 26.5 (385) | 26.2 (380) | 26.2 (380) | 25.9 (375) | 25.9 (375) | 25.9 (375) | 25.9 (375) | 25.9 (375) |
| Total Mass Flow Rate, kg/h (lb/h) | 289497.2 (638232) | 289497.2 (638232) | 289497.2 (638232) | 81316 (179271) | 81316 (179271) | 421369.6 (928961) | 421369.6 (928961) | 213188.4 (470000) | 208181.2 (458961) |
| Water, kg/h (lb/h) | 0 (0) | 0 (0) | 0 (0) | 81307.2 (179251.6) | 81307.2 (179251.6) | 0.004 (0.01) | 0.004 (0.01) | 0.002 (0.005) | 0.002 (0.005) |
| Methanol, kg/h (lb/h) | 289497.2 (638232) | 289497.2 (638232) | 289497.2 (638232) | 5.3 (11.6) | 5.3 (11.6) | 535.1 (1179.8) | 535.1 (1179.8) | 270.8 (597.0) | 264.4 (582.9) |
| Dimethyl ether kg/h, (lb/h) | 0 (0) | 0 (0) | 0 (0) | 3.6 (7.9) | 3.6 (7.9) | 420834.4 (927781.1) | 420834.4 (927781.1) | 212917.6 (469403) | 207916.8 (458378) |
| Mass Fraction | | | | | | | | | |
| Water | 0 | 0 | 0 | ~1 | ~1 | trace | trace | trace | trace |
| Methanol | 1 | 1 | 1 | trace | trace | 0.001 | 0.001 | 0.001 | 0.001 |
| Dimethyl Ether | 0 | 0 | 0 | trace | trace | 0.999 | 0.999 | 0.999 | 0.999 |

Operation of distillation column reactor 502 as described above results in substantially complete conversion of the methanol and the recovery of an essentially pure overhead dimethyl ether fraction 521 and an essentially pure bottoms water fraction 530, as shown in Table 2. Operating conditions are selected to result in the methanol feed being essentially trapped in the column, the overheads being at a temperature less than the boiling point of methanol, and the bottoms being at a temperature greater than the boiling point of methanol. By weight, approximately 99.9 percent conversion of the methanol is obtained and essentially pure dimethyl ether and water fractions are recovered in the overhead and bottoms streams, 521 and 530, respectively.

Although the examples above describe the use of a single distillation column reactor, side reactors and pre-reactors may also be used, as described above. One potential benefit of a pre-reactor is that a lower activity catalyst may be used in the distillation column reactor system, thus allowing for a longer catalyst life for the catalyst disposed in the distillation column reactor. One or more fixed bed reactors may contain a higher activity catalyst that may be regenerated or replaced more readily, the process thus potentially allowing for complete conversion of alcohol, recovering substantially pure product streams, and extended distillation column reactor catalyst life.

Embodiments disclosed herein may provide for the effective conversion of alkyl alcohols to dialkyl ethers. Advantageously, various embodiments may provide for one or more of substantially complete conversion of the alcohol, recovery of an essentially pure ether fraction, and recovery of an essentially pure water fraction.

Additionally, embodiments disclosed herein may provide for a simplified process for the production of dialkyl ethers. Advantageously, embodiments disclosed herein may provide for reduced piece count, decreased need for downstream separation or purification processes, reduced capital and/or operating expense, and other advantages.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of dialkyl ether, the process comprising:
    feeding a stream comprising an alkyl alcohol to a distillation column reactor system;
    concurrently in the distillation column reactor system:
        i) contacting the alkyl alcohol with a catalytic distillation structure in a distillation reaction zone thereby catalytically dehydrating at least a portion of the alkyl alcohol to form a corresponding dialkyl ether and water; and
        ii) fractionating the resulting dialkyl ether from the water;
    operating the distillation column reactor system to obtain substantially complete conversion of the alkyl alcohol to form the corresponding dialkyl ether and water;
    recovering the dialkyl ether from the distillation column reactor as an overheads fraction, wherein the overheads comprises at least about 99.5 weight percent dialkyl ether;
    recovering the water from the distillation column reactor as a bottoms fraction, wherein the bottoms comprises at least about 99.5 weight percent water; and
    wherein the operating comprises:
        maintaining the distillation reaction zone at a temperature in the range from about 120° C. to about 260° C.;
        maintaining the distillation reaction zone at a pressure in the range from about 15 bar to about 45 bar; and
        maintaining a reflux ratio from about 0.5 to about 10.

2. The process of claim 1, wherein the operating comprises adjusting at least one of a column temperature, a column pressure, a feed rate, and a reflux rate.

3. The process of claim 1, wherein the operating comprises:
    maintaining a temperature profile across the reaction zone to satisfy the kinetics of the dehydration reaction; and
    maintaining a reflux rate above the reaction zone to separate the dialkyl ether from unreacted alkyl alcohol.

4. The process of claim 1, further comprising:
    contacting the alkyl alcohol with a catalyst in a fixed bed reaction zone thereby catalytically reacting at least a portion of the alkyl alcohol to form a mixture comprising the corresponding dialkyl ether, water, and unreacted alkyl alcohol;
    using the resulting mixture in the feeding.

5. The process of claim 4, further comprising operating the fixed bed reaction zone at a boiling point of the mixture.

6. The process of claim 4, wherein the catalytic distillation reactor system comprises a divided wall column comprising at least one catalyst containing zone, and wherein the feeding is to a non-catalytic portion of the distillation column reactor.

7. The process of claim 4, wherein the catalytic distillation reactor system comprises a distillation column and a side column comprising the distillation reaction zone.

8. The process of claim 4, wherein the catalytic distillation reactor system comprises a distillation column reactor comprising the distillation reaction zone.

9. The process of claim 1, wherein the catalytic distillation reactor system comprises a distillation column reactor comprising the distillation reaction zone.

10. The process of claim 4, wherein a catalyst in the fixed bed reaction zone has a higher activity than a catalyst in the distillation reaction zone.

11. The process of claim 10, wherein the fixed bed catalyst comprises at least one of a metal-treated zeolite, a hydrofluoric acid-treated clay, and a silica-alumina.

12. The process of claim 11, wherein the distillation reaction catalyst comprises at least one of a metalized resin and silica-alumina.

13. The process of claim 1, wherein the overheads comprises at least about 99.8 weight percent dialkyl ether.

14. The process of claim 1, wherein the bottoms comprises at least about 99.8 weight percent water.

15. The process of claim 1, wherein the alkyl alcohol comprises at least one of methanol and ethanol.

* * * * *